(12) United States Patent
Knaup et al.

(10) Patent No.: US 7,935,831 B2
(45) Date of Patent: May 3, 2011

(54) PROCESS FOR THE PREPARATION OF 2-AZABICYCLO[3.3.0]OCTANE-3-CARBOXYLIC ACID DERIVATIVES

(75) Inventors: Günter Knaup, Bruchköbel (DE); Milan Latinovic, Nidda (DE)

(73) Assignee: Evonik Degussa GmbH, Essen (DE)

( * ) Notice: Subject to any disclaimer, the term of this patent is extended or adjusted under 35 U.S.C. 154(b) by 718 days.

(21) Appl. No.: 11/886,420

(22) PCT Filed: Mar. 2, 2006

(86) PCT No.: PCT/EP2006/060406
§ 371 (c)(1),
(2), (4) Date: Jan. 12, 2009

(87) PCT Pub. No.: WO2006/100168
PCT Pub. Date: Sep. 28, 2006

(65) Prior Publication Data
US 2009/0306404 A1    Dec. 10, 2009

(30) Foreign Application Priority Data
Mar. 19, 2005   (DE) .......................... 10 2005 012 771

(51) Int. Cl.
C07D 209/52    (2006.01)
C07C 271/02    (2006.01)
C07C 271/22    (2006.01)

(52) U.S. Cl. ....................................... 548/452; 560/115

(58) Field of Classification Search .................. 548/452; 560/115
See application file for complete search history.

(56) References Cited

U.S. PATENT DOCUMENTS
4,727,160 A    2/1988   Teetz et al.

OTHER PUBLICATIONS

International Search Report for PCT/EP2006/060406.
Written Opinion of the International Searching Authority for PCT/EP2006/060406.
Henning, et al., "Synthesis of Esters of Lipophilic Proline Analogs by Reduction of Ethyl 5,6-Dihydro-4H-1,2-oxazine-3-carboxylates," *Synthesis* 4:265-268 (Apr. 1989).
Mota, et al., "New Diastereoselective Route to 2-Substituted cis-(2S,5S)- and trans-(2S,5S)-5- Alkylpyrrolidines as Indolizidine and Pyrrolizidine Scaffolds," *Eur. J. Org. Chem.* 4187-4198 (2003).
Collier, et al., "Hydroboration-Suzuki cross coupling of unsaturated amino acids; the synthesis of pyrimidine derivatives," *Tetrahedron* 58:6117-6125 (2002).

International Preliminary Report on Patentability issued Sep. 25, 2007 for PCT/EP2006/060406.

*Primary Examiner* — Jason M Nolan
(74) *Attorney, Agent, or Firm* — Law Office of Michael A. Sanzo, LLC

(57) ABSTRACT

The present invention is aimed at a process for the preparation of compounds of the general formula (I).

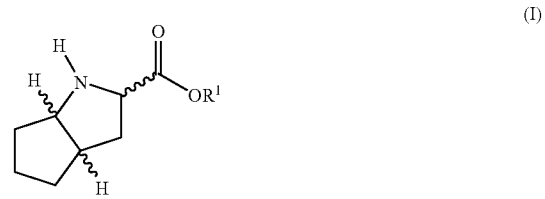

The objective process is in this case based on the Michael reaction of compounds of the general formula (III)

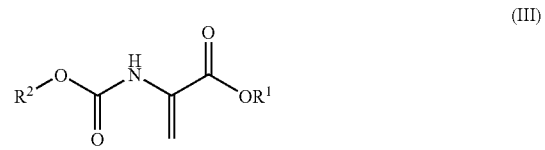

with compounds of the general formula (IV),

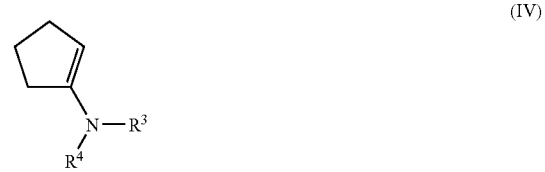

with subsequent hydrogenation and cyclization of the intermediates of the formula (II) obtained.

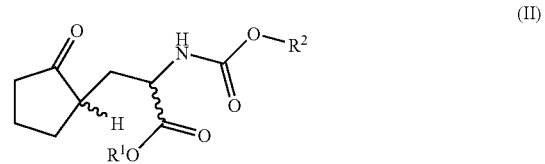

20 Claims, No Drawings

PROCESS FOR THE PREPARATION OF 2-AZABICYCLO[3.3.0]OCTANE-3-CARBOXYLIC ACID DERIVATIVES

CROSS REFERENCE TO RELATED APPLICATIONS

The present application represents U.S. national stage of international application PCT/EP2006/060406, which had an international filing date of Mar. 2, 2006, and which was published in English under PCT Article 21(2) on Sep. 28, 2006. Priority is claimed through the international application to German application 10 2005 012 771.1, filed on Mar. 19, 2005. These prior applications are incorporated in their entirety herein by reference.

The present invention is aimed at a process for the preparation of compounds of the general formula (I).

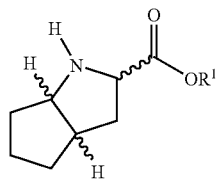

Compounds of this type are valuable intermediates for the preparation of bioactive agents. 2-Azabicyclo-[3.3.0]-octane-3-carboxylic acids are used, for example, for the preparation of Ramipril® (N-(1-(S)-ethoxycarbonyl-3-phenyl-propyl)-(S)-alanyl-(S)-cis,endo-2-azabicyclo-[3.3.0]-octane-3-S-carboxylic acid), an ACE inhibitor (A. Kleemann, J. Engel, Pharmaceutical Substances, 4th Edition, page 1785, Thieme Verlag Stuttgart, 2001).

A large number of processes for the preparation of racemic 2-azabicyclo-[3.3.0]-octane-3-carboxylic acids have been described, such as, for example:
  Anodic oxidation of N-acylcyclopentapyrroles and subsequent cyanation and hydrolysis (DE 3151690)
  Starting from bicyclo-[3.3.0]-nonan-2-one by Beckmann rearrangement, halogenation and Favorskii rearrangement (DE 3151690)
  Starting from cyclopentene via organomercury compounds (DE 3300316, R. Henning, H. Urbach, Tetrahdron Letters, 24, 5343-6 (1983)).
  Starting from bromocyclopentane and serine and intramolecular cyclization of an intermediate iodoalanine with $Bu_3SnH$ (DE 297620, H. Urbach, R. Henning, Hetetero-cycles 28, 957-65 (1989).
  By hydrogenation of tetrahydrocyclopentapyrrole-2-carboxylic acid (WO86/00896, U.S. Pat. No. 4,587,258).
  By 1,3-dipolar cycloaddition of azomethines (L. M. Harwood, L.C. Kitchen, Tetrahedron Lett., 34, 6603 (1993)).

The presumably preferred process ((A. Kleemann, J. Engel, Pharmaceutical Substances, 4th edition, page 1785, Thieme Verlag Stuttgart, 2001); EP 79022; V. Teetz, R. Geiger, H. Gaul, Tetrahedron Letters, 25, 4479-82 (1984)) consists in first preparing methyl 2-acetamino-3-chloropropionate from serine in a 3-stage reaction sequence (DE 19941062). This is reacted with pyrrolidinocyclopentene to give methyl cyclo-pentanonylacetamidopropionate. With the aid of strong acids, this is cyclized with cleavage of the acylamide and ester group to give the bicyclic iminoester. Subsequent catalytic hydrogenation then yields racemic 2-azabicyclo-[3.3.0]-octane-3-carboxylic acid. The reaction sequence is shown in Scheme 1:

Scheme 1:

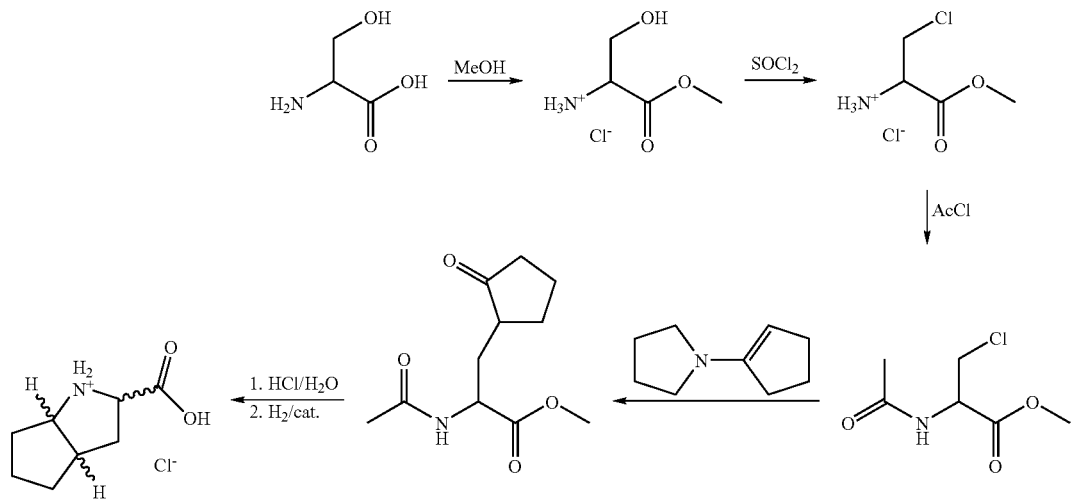

The 2-azabicyclo-[3.3.0]-octane-3-carboxylic acid is formed mainly in the cis-endo conformation, i.e. mainly a mixture of the RRR- and SSS-compounds results. For resolution of racemates, the carboxylic acid is converted to an ester, preferably the benzyl ester. This is cleaved into the diastereomerically pure bicycles by salt formation with a chiral acid. O,O-diacyltartaric acids (DE 3345355), optically active N-acyl-amino acids (EP 115345) and mandelic acid (J. Martens, S. Lübben, Journal f. prakt. Chemie, 332, 1111-1117 (1990)) are described as chiral acids.

In order to make possible selective removal of the ester group in the finished active agent Ramipril, the benzyl ester is employed for the coupling and therefore preferably also for the resolution of racemates.

In the preferred process (Kleemann Engel, V. Teetz, R. Geiger, H. Gaul, Tetrahdron Letters, 25, 4479-82 (1984)), the resolution of racemates of the benzyl ester is carried out with the aid of N-benzyloxycarbonyl-L-phenylalanine (Z-L-Phe-OH). The coupling of the SSS-benzyl ester with N-(1-(S)-ethoxycarbonyl-3-phenylpropyl)-(S)-alanine (NEPA) and subsequent removal of the benzyl ester by hydrogenation finally yields Ramipril (Scheme 2).

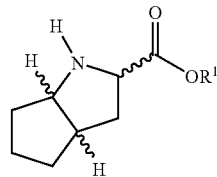
(I)

Scheme 2:

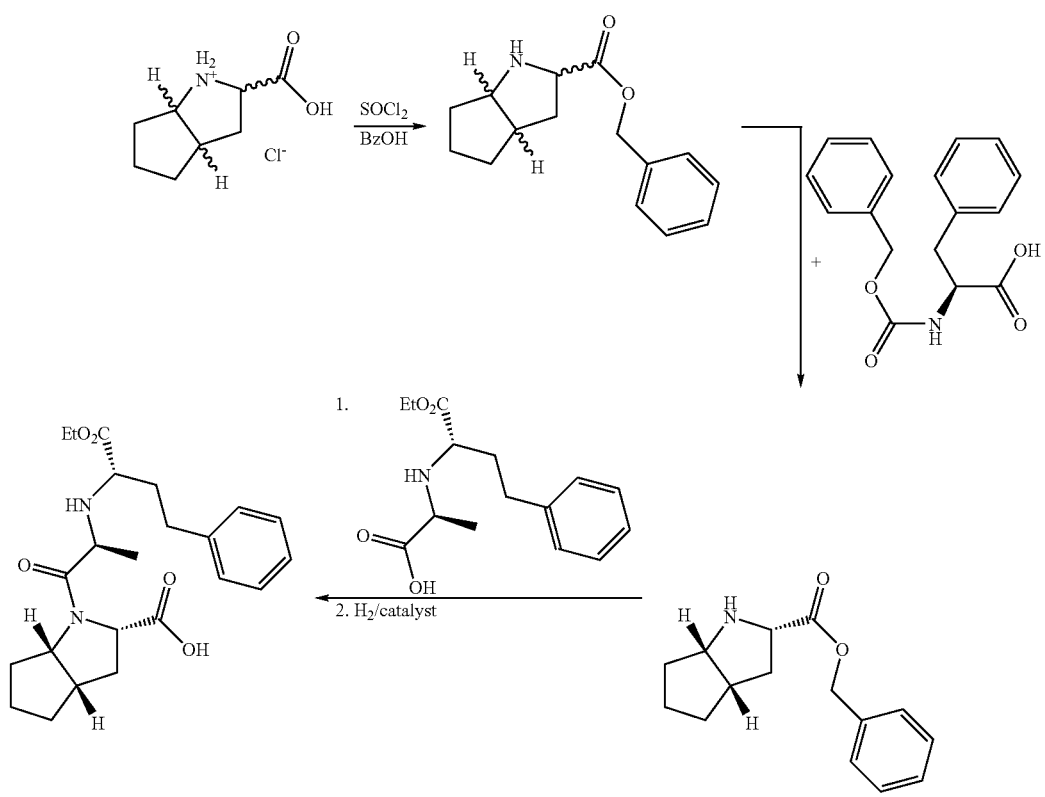

It was the object of the present invention to make available an improved process compared with the prior art for the preparation of intermediates of the general formula (I). In particular, it is important that the process can be carried out advantageously on the industrial scale and, seen from the economic as well as ecological point of view, that it is superior to the processes of the prior art.

The object is achieved according to the claims. Claims 1 to 4 are aimed at a preferred process for the preparation of compounds of the general formula (I). Claim 4 protects novel intermediate compounds of the general formula (II). Claims 5 to 7 comprise a process according to the invention for the preparation of compounds of the general formula (II).

As a result of hydrogenating in the presence of a catalyst, in a process for the preparation of compounds of the general formula (I) or its salts, in which
$R^1$ is H, $(C_1-C_8)$-alkyl, $(C_6-C_{18})$-aryl, $(C_7-C_{19})$-aralkyl, $(C_1-C_8)$-alkyl-$(C_6-C_{18})$-aryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl,
a compound of the general formula (II),

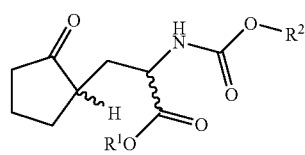
(II)

in which
$R^1$ is formed as indicated above and
$R^2$ is a hydrogenolytically cleavable group, the object set is achieved exceedingly advantageously, but for that no less expectedly. As a result of the fact that, in the compound of the general formula (II), the radical R² is a hydrogenolytically cleavable group, the person skilled in the art obtains in a surprisingly simple manner in one step compounds of the general formula (I), which can immediately be employed in the subsequent conventional resolution of racemates without further double decomposition steps or esterifications having to be carried out. It was thus not foreseeable against the background of the prior art that the three chemical steps (cleavage of the N-protective group, cyclization and hydrogenation) can proceed so advantageously in one process step.

In the context of the breadth of variation of the radicals indicated above, the person skilled in the art is free to choose those which, seen from the cost/benefit ratio, appear particularly advantageous. As the radical R¹, advantageously H or $(C_1-C_8)$-alkyl is employed, R² can optionally be ring-substituted benzyl. A radical R¹ such as methyl or ethyl is preferred. Benzyl can preferably be employed as R².

For the process according to the invention, the person skilled in the art can use various organic solvents suitable for him. Advantageous organic solvents are those which dissolve the products employed to an adequate extent and otherwise prove inert to the reaction. Preferred organic solvents are accordingly those selected from the group consisting of alcohols, such as, for example, methanol, ethanol, isopropanol, ethers, such as, for example, disopropyl ether, methyl tert-butyl ether, dimethoxyethane, THF, aromatics, such as, for example, toluene, xylene, carboxylic acid esters such as, for example, ethyl acetate, isopropyl acetate, n-butyl acetate, secondary amides such as, for example, DMF, NMP. The use of alcohols which correspond to the radical R¹ is very particularly preferred. Thus ethanol or methanol is highly preferred as a solvent.

The objective process can be carried out analogously to expert knowledge. As a catalyst, those catalysts are preferably employed which are capable of bringing about the hydrogenation of C=C and C=N double bonds respectively and the hydrogenolytic cleavage of the radicals indicated above. Possible catalysts are both heterogeneous and homogeneous catalysts, in particular those selected from the group consisting of palladium, platinum, rhodium, nickel, cobalt or the catalysts mentioned for this purpose in Houben-Weyl, Methoden der Organischen Chemie [Methods of Organic Chemistry], Volume 4/1c, pages 14-480, Thieme Verlag Stuttgart, 1974.

The hydrogenation is advantageously carried out at a temperature of 0-100° C., preferably 10-80° C., particularly preferably at 20-30° C.

The hydrogen pressure can be adjusted during the reaction according to the values suitable to the person skilled in the art. The pressure is preferably 1 to 50 bar, preferably 1 to 30 bar, more preferably 1 to 20 bar.

The hydrogenation according to the invention can be carried out conventionally using elemental hydrogen. It can, however, also on principle be run in the form of transfer hydrogenation, according to the manner known to the person skilled in the art (Houben-Weyl, Methoden der Organischen Chemie, Volume 4/1c, pages 67-76, Thieme Verlag Stuttgart, 1974).

The subject of the present invention is likewise a compound of the general formula (II) or, if R¹=H, its salts

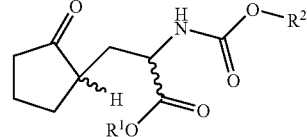

(II)

in which
R¹ is H, $(C_1-C_8)$-alkyl, $(C_6-C_{18})$-aryl, $(C_7-C_{19})$-aralkyl, $(C_1-C_8)$-alkyl-$(C_6-C_{18})$-aryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl and
R² is a hydrogenolytically cleavable group. These compounds indicated here are advantageous intermediates for the preparation of the compound of the general formula (I). The preferred embodiments indicated above for the radicals R¹ and R² analogously apply here.

In a last embodiment, the present invention is concerned with the preparation of compounds of the general formula (II). These are prepared advantageously in a process according to the invention in which compounds of the general formula (III)

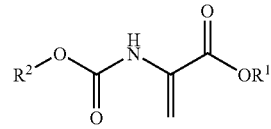

(III)

in which
R¹ and R² assume the meaning indicated above, are reacted with enamines of the general formula (IV)

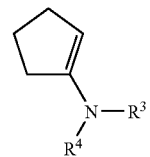

(IV)

in which
R³ and R⁴ independently of one another can be $(C_1-C_8)$-alkyl, $(C_6-C_{18})$-aryl, $(C_7-C_{19})$-aralkyl, $(C_1-C_8)$-alkyl-$(C_6-C_{18})$-aryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl or R³ and R⁴ together form a $(C_2-C_5)$-alkylene bridge optionally containing heteroatoms. Here too, the preferred embodiments already just mentioned apply again for the radicals R¹ and R². Preferred embodiments for the radicals R³ and R⁴ are those selected from the group in which the radicals R³ and R⁴ form a 5- or 6-membered heterocycle with the nitrogen atom. Compounds of the formula (IV) are very particularly preferred in which the radicals R³ and R⁴, together with the nitrogen atom, are pyrrolidine, piperidine or morpholine.

Advantageously, the process according to the invention mentioned here is carried out in organic solvents. Those which are preferably suitable are: ethers, such as, for example, disopropyl ether, methyl tert-butyl ether, dimethoxyethane, THF, aromatics, such as, for example, toluene, xylene, carboxylic acid esters such as, for example, ethyl acetate, isopropyl acetate, n-butyl acetate, secondary amides such as, for example, DMF, NMP, chlorinated hydrocarbons such as chloroform, methylene chloride. Halogenated organic solvents are very particularly preferred in this connection. Chloroform or methylene chloride is highly preferably employed.

The reaction of the compounds of the general formula (IV) with the compounds of the general formula (III) can preferably be carried out at temperatures between 0-100° C., preferably 10-50° C., very particularly preferably between 15-30° C.

According to the invention, in the preparation of the compounds of the general formula (I) the procedure is as follows. In analogy to N-acyl derivatives (M. Bergmann, K. Grafe, Hoppe-Seylers Zeitschrift Physiologische Chem. 187, 187 (1930)), the urethanes of the formula (III) can be prepared from the simply accessible compounds of the formula (V)

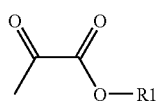
(V)

and the likewise simply accessible urethanes of the formula (VI)

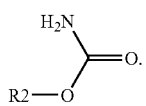
(VI)

For the radicals $R^1$ and $R^2$, the definitions indicated above consequently apply. The use of ethyl pyruvate and benzyl-urethane is highly preferred in this connection. The reaction is preferably carried out in such a way that the resulting water of reaction is removed by azeotropic distillation. A particularly suitable solvent for this is toluene. The person skilled in the art, however, knows further suitable solvents for this case.

The compounds of the formula (III) can be obtained without further purification in a purity sufficient for the subsequent reactions. In order to avoid unintentional polymerization of the acrylic acid derivatives of the formula (III), free radical scavengers, preferably hydroquinones, are added. The compounds of the general formula (III) can subsequently be added to compounds of the general formula (II) as described in a Michael reaction to give compounds of the general formula (IV). In the subsequent hydrogenation, the N-protective group is cleaved and the compound cyclized to give (I).

In contrast to the process described in EP 79022, the addition of strong acids is not necessary for the reaction. The cleavage of the N-protective group is carried out in situ in the process according to the invention by catalytic hydrogenation. The intermediates of the formula (II) resulting thereby, which are very unstable in free form, in which $R^2$ is H, cyclize spontaneously. Use of strong acids, as required according to the prior art (EP 79022), is not necessary.

A further advantage of the process according to the invention consists in the fact that the products of the formula (I), in which $R^1$ is not H, do not have to be subjected directly to resolution of racemates with optically active acids such as, for example, N-benzyloxycarbonyl-L-phenyl-alanine, as the ester group is retained. Fresh esterifi-cation, as described in EP 79022, is unnecessary. If the hydrogenation is moreover carried out without addition of acids, the esters of the formula (I) are obtained as free bases and can be reacted directly with optically active acids without further purification.

The diastereomerically pure salts thus obtained of the 2-azabicyclo-[3.3.0]-octane-3-carboxylic acids prepared according to this invention can be resolved into their components in a known manner. The enantiomerically enriched 2-azabicyclo-[3.3.0]-octane-3-carboxylic acid esters thereby obtained can be converted to the corresponding free acid by acidic hydrolysis. The release is preferably carried out such that the (S)-cis-endo-2-azabicyclo-[3.3.0]-octane-3-carboxylic acid ester is dissolved in water at acidic pH and the optically active auxiliary acid obtained is extracted with an organic solvent and recycled. The ester can then be cleaved by heating the acidic aqueous solution. The 2-azabicyclo-[3.3.0]-octane-3-carboxylic acid can preferably be isolated as an internal salt, but preferably as the hydrochloride, by evaporating the reaction solution. The (S)-cis-endo-2-azabicyclo-[3.3.0]-octane-3-carboxylic acid can be reacted according to known methods (see above) with N-(1-(S)-ethoxycarbonyl-3-phenylpropoyl)-(S)-alanine (NEPA) to give Ramipril®.

The objective process thus helps to considerably simplify the synthesis of the bioactive agent Ramipril® for the industrial scale. This simplification was not automatically to be expected against the background of the prior art, on the contrary the intermediates formed during the reaction are very reactive intermediate compounds which are capable of entering into many side reactions, such as, for example, polymerization. Consequently, it can surprisingly be true that, in spite of this danger, the described combination of three chemical reaction steps in one process step is possible.

$(C_1-C_8)$-Alkyl radicals are to be regarded as methyl, ethyl, n-propyl, isopropyl, n-butyl, isobutyl, sec-butyl, tert-butyl, pentyl, hexyl, heptyl or octyl along with all of their bonding isomers.

The radical $(C_1-C_8)$-alkoxy corresponds to the radical $(C_1-C_8)$-alkyl with the proviso that this is bonded to the molecule via an oxygen atom.

$(C_2-C_8)$-alkoxyalkyl are intended as radicals in which the alkyl chain is interrupted by at least one oxygen function, it not being possible for two oxygen atoms to be bonded to one another. The number of carbon atoms indicates the total number of carbon atoms contained in the radical.

A $(C_3-C_5)$-alkylene bridge is a carbon chain with three to five C atoms, this chain being bonded to the molecule considered via two different C atoms.

The radicals described in the preceding paragraphs can be mono- or polysubstituted by halogens and/or N, O, P, S, Si atom-containing radicals. These are, in particular, alkyl radicals of the abovementioned type, which contain one or more of these heteroatoms in their chain or which are bonded to the molecule via one of these heteroatoms.

$(C_3-C_8)$-Cycloalkyl is understood as meaning cyclopropyl, cyclobutyl, cyclopentyl, cyclohexyl or cycloheptyl radicals etc. These can be substituted by one or more halogens and/or N, O, P, S, Si atom-containing radicals and/or contain N, O, P, S atoms in the ring, such as, for example, 1-, 2-, 3-, 4-piperidyl, 1-, 2-, 3-pyrrolidinyl, 2-, 3-tetrahydrofuryl, 2-, 3-, 4-morpholinyl.

A $(C_3-C_8)$-cycloalkyl-$(C_1-C_8)$-alkyl radical is a cycloalkyl radical such as shown above, which is bonded to the molecule via an alkyl radical such as indicated above.

$(C_1-C_8)$-Acyloxy is, in the context of the invention, an alkyl radical such as defined above having at most 8 C atoms, which is bonded to the molecule via a COO— function.

($C_1$-$C_8$)-Acyl is, in the context of the invention, an alkyl radical such as defined above having at most 8 C atoms, which is bonded to the molecule via a CO— function.

A ($C_6$-$C_{18}$)-aryl radical is understood as meaning an aromatic radical having 6 to 18 C atoms. In particular, included in this are compounds such as phenyl, naphthyl, anthryl, phenanthryl or biphenyl radicals or systems of the pre-described type fused to the molecule concerned, such as, for example, indenyl systems, which can optionally be substituted by halogen, ($C_1$-$C_8$)-alkyl, ($C_1$-$C_8$)-alkoxy, $NH_2$, $NH(C_1$-$C_8)$-alkyl, $N((C_1$-$C_8)$-alkyl$)_2$, OH, $CF_3$, $NH(C_1$-$C_8)$-acyl, $N((C_1$-$C_8)$-acyl$)_2$, ($C_1$-$C_8$)-acyl, ($C_1$-$C_8$)-acyloxy.

A ($C_7$-$C_{19}$)-aralkyl radical is a ($C_6$-$C_{18}$)-aryl radical bonded to the molecule via a ($C_1$-$C_8$)-alkyl radical.

A ($C_3$-$C_{18}$)-heteroaryl radical is, in the context of the invention, a five-, six- or seven-membered aromatic ring system of 3 to 18 C atoms, which contains heteroatoms such as, for example, nitrogen, oxygen or sulphur in the ring. Such heteroatoms are in particular regarded as being radicals such as 1-, 2-, 3-furyl, 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. This radical can be substituted by the same radicals as the abovementioned aryl radical.

A ($C_4$-$C_{19}$)-heteroaralkyl is understood as meaning a hetero-aromatic system corresponding to the ($C_7$-$C_{19}$)-aralkyl radical.

Suitable halogens (Hal) are fluorine, chlorine, bromine and iodine.

N-Protective groups are to be understood as meaning protective groups which generally are customarily employed in amino acid chemistry for the protection of nitrogen atoms. Those which may particularly be mentioned are: formyl, acetyl, Moc, Eoc, phthalyl, Boc, Alloc, Z, Fmoc, etc.

A hydrogenolytically cleavable group is preferably such an N-protective group selected from the group consisting of optionally ring-substituted benzyl. Suitable ring-substituted variants are preferably 4-substituted halogen, nitro, alkyl or alkoxy derivatives (Houben-Weyl, Methoden der Organischen Chemie, Volume 15/1, page 69, Thieme Verlag Stuttgart, 1974).

The term enantiomerically enriched or enantiomeric excess is understood in the context of the invention as meaning the proportion of an enantiomer in the mixture with its optical antipodes in a range of >50% and <100%. The ee value is calculated as follows:

([enantiomer1)]-[enantiomer2])/([enantiomer1]+
[enantiomer2])=ee value

The naming of the chemical compounds appearing in the text comprises, in the context of the invention, all possible diastereomers, it also being intended to name the two optical antipodes of a respective diastereomer.

The references mentioned in this specification are regarded as being comprised in the disclosure.

EXAMPLES

Ethyl N-benzyloxycarbonyl-2-aminoacrylate 288 g of ethyl pyruvate, 250 g of benzylurethane, 2.5 g of p-toluenesulphonic acid and 1 g of hydroquinone are introduced into 2.5 l of toluene and refluxed for 9 h in a water separator. The reaction solution is then filtered through silica gel and washed with 500 ml of toluene. The filtrate is treated with 1 g of hydroquinone and concentrated to the greatest possible extent on a rotary evaporator. 376 g of ethyl N-benzyloxycarbonyl-2-amino-acrylate are obtained as an oil, which according to HPLC has a purity of about 90%.

$^1$H-NMR (DMSO-$D_6$): 1.23 (t, 3H), 4.18 (q, 2H), 5.11 (s, 2H), 5.61 (s, 1H), 5.78 (s, 1H), 7.37 (m, 5H), 8.86 (s, 1H).

Ethyl 2-N-benzyloxycarbonylamino-3-(2-oxocyclopentyl)-propionate 366 g of ethyl N-benzyloxycarbonyl-2-aminoacrylate (about 90% strength) and 191 g of cyclopentenopyrrolidine are dissolved in $CH_2Cl_2$ and the solution is stirred for 16 hours at room temperature. The reaction solution is subsequently treated with 350 ml of acetic acid and 1 l of water and intensively stirred for 15 min. After phase separation, the organic phase is again extracted with a mixture of 180 ml of acetic acid and 1 l of water and subsequently washed with 500 ml of water. The solution is then filtered through silica gel and subsequently completely evaporated in vacuo. 463 g of ethyl 2-N-benzyloxycarbonylamino-3-(2-oxocyclopentyl)propionate are obtained as an oil.

$^1$H-NMR (DMSO-$D_6$): 1.17 (m, 3H), 1.51 (m, 2H), 1.69 (m, 1H), 1.90 (m, 1H), 2.09 (m, 5H), 4.09 (m, 2H), 4.24 (m, 1H, main rotamer), 5.05 (s, 2H, main rotamer), 7.34 (m, 5H), 7.75 (d, 1H, main rotamer).

Ethyl cis-2-azabicyclo-[3.3.0]-octane-3-carboxylate 200 g of ethyl 2-N-benzyloxycarbonylamino-3-(2-oxocyclo-pentyl)propionate is dissolved in 1000 ml of ethanol, treated with 5 g of catalyst (5% palladium on activated carbon) and subsequently hydrogenated at 5 bar. After 4 hours, starting material is no longer detectable by HPLC. The catalyst is filtered and the filtrate is concentrated to the greatest possible extent. 103 g of ethyl cis-2-aza-bicyclo-[3.3.0]-octane-3-carboxylate are obtained as a yellowish-coloured oil, which is reacted further without further purification. According to the $^1$H-NMR spectrum, the proportion of cis-endo isomer is 78 mol %.

$^1$H-NMR (DMSO-$D_6$, main isomer): 1.18 (t, 3H), 1.30 (m, 1H), 1.51 (m, 6H), 2.19 (m, 1H), 2.48 (m, 1H), 3.50 (dd, 1H), 3.53 (m, 1H), 4.07 (dq, 2H).

Ethyl(S)-cis-endo-2-azabicyclo-[3.3.0]-octane-3-carboxylate Z-L-phenylalanine salt 100 g of the ethyl cis-2-azabicyclo-[3.3.0]-octane-3-carboxylate prepared in Example 3 are treated with a solution of 84 g of N-benzyloxycarbonyl-L-phenylalanine in 200 ml of ethyl acetate which is prepared hot. 1 l of MTBE is added to the clear solution. After seeding, it is stirred for 4 hours at room temperature, the suspension becoming viscous.

The product is filtered off and washed twice with 100 ml of MTBE. After drying at 50° C. in vacuo, 66.4 g of ethyl(S)-cis-endo-2-azabicyclo-[3.3.0]-octane-3-carboxylate Z-L-phenylalanine salt are obtained.

$^1$H-NMR (DMSO-$D_6$): 1.18 (t, 3H), 1.33 (m, 1H), 1.37 (m, 1H), 1.54 (m, 5H), 2.21 (m, 1H), 2.94 (ddd, 2H), 3.57 (m, 2H), 4.08 (dq, 2H), 4.15 (m, 1H), 4.97 (s, 2H), 7.27 (m, 5H), 7.46 (d, 1H).

(S)-cis-endo-2-Azabicyclo-[3.3.0]-octane-3-carboxylic acid hydrochloride 3.0 g of ethyl(S)-cis-endo-2-azabicyclo-[3.3.0]-octane-3-carboxylate Z-L-phenylalanine salt are suspended in 20 ml of water and 40 ml of MTBE. After addition of 1 ml of 37% strength hydrochloric acid, the mixture is stirred until a clear solution results. The aqueous phase is separated off and again extracted with 40 ml of MTBE. It is then briefly stripped in vacuo, treated with 14 ml of 37% strength hydrochloric acid and heated for 14 hours at 100-105° C. The mixture is then evaporated in vacuo, and the residue is treated with 10 ml of acetic acid and evaporated again. The residue is then dissolved in 10 ml of acetic acid and crystallized by addition of MTBE. 0.95 g of (S)-cis-endo-2-azabicyclo-[3.3.0]-octane-3-carboxylic acid hydrochloride is obtained.

$^1$H-NMR (DMSO-$D_6$): 1.45 (m, 1H), 1.60 (m, 3H), 1.74 (m, 2H), 1.99 (m, 1H), 2.45 (m, 1H), 2.80 (m, 1H), 3.98 (m, 1H), 4.21 (dd, 1H), 8.70 (s, broad, 1H), 10.60 (s, broad, 1H), 13.80 (s, broad, 1H).

The invention claimed is:

1. A process for the preparation of compounds of the general formula (I) or their salts,

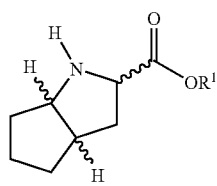

wherein:
$R^1$ is H, ($C_1$-$C_8$)-alkyl, ($C_6$-$C_{18}$)-aryl, ($C_7$-$C_{19}$)-aralkyl, ($C_1$-$C_8$)-alkyl-($C_6$-$C_{18}$)-aryl, ($C_3$-$C_8$)-cycloalkyl, ($C_1$-$C_8$)-alkyl-($C_3$-$C_8$)-cycloalkyl, ($C_3$-$C_8$)-cycloalkyl-($C_1$-$C_8$)-alkyl, said process comprising hydrogenating a compound of general formula II in the presence of a catalyst:

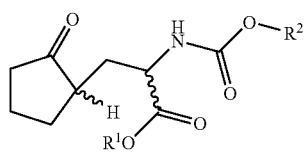

wherein
$R^1$ is as described above and
$R^2$ is a hydrogenolytically cleavable group.

2. The process of claim 1, wherein:
$R^1$ is H or ($C_1$-$C_8$)-alkyl, and
$R^2$ is a benzyl that is optionally ring-substituted.

3. The process of claim 1, wherein the hydrogenation reaction is carried out in an alcohol solvent.

4. The process of claim 2 wherein the hydrogenation reaction is carried out in an alcohol solvent.

5. A compound of the general formula (II) or, if $R^1$=H, its salts

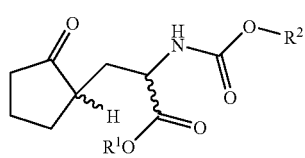

wherein:
$R^1$ is H, ($C_1$-$C_8$)-alkyl, ($C_6$-$C_{18}$)-aryl, ($C_7$-$C_{19}$)-aralkyl, ($C_1$-$C_8$)-alkyl-($C_6$-$C_{18}$)-aryl, ($C_3$-$C_8$)-cycloalkyl, ($C_1$-$C_8$)-alkyl-($C_3$-$C_8$)-cycloalkyl, ($C_3$-$C_8$)-cycloalkyl-($C_1$-$C_8$)-alkyl and $R^2$ is a hydrogenolytically cleavable group.

6. The compound of claim 5, wherein $R^1$ is H.

7. The compound of claim 5, wherein $R^1$ is a ($C_1$-$C_8$)-alkyl.

8. The compound of claim 5, wherein $R^1$ is a ($C_6$-$C_{18}$)-aryl.

9. The compound of claim 5, wherein $R^1$ is a ($C_7$-$C_{19}$)-aralkyl.

10. The compound of claim 5, wherein $R^1$ is a ($C_1$-$C_8$)-alkyl-($C_6$-$C_{18}$)-aryl.

11. The compound of claim 5, wherein $R^1$ is a ($C_3$-$C_8$)-cycloalkyl.

12. The compound of claim 5, wherein $R^1$ is a ($C_1$-$C_8$)-alkyl-($C_3$-$C_8$)-cycloalkyl.

13. The compound of claim 5, wherein $R^1$ is a ($C_3$-$C_8$)-cycloalkyl-($C_1$-$C_8$)-alkyl.

14. A process for the preparation of compounds according to claim 5, comprising reacting compounds of the general formula (III)

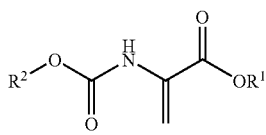

wherein $R^1$ and $R^2$ are as defined in claim 5, with enamines of the general formula (IV)

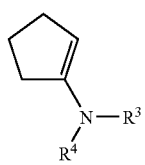

wherein:
$R^3$ and $R^4$ independently of one another can be ($C_1$-$C_8$)-alkyl, ($C_6$-$C_{18}$)-aryl, ($C_7$-$C_{19}$)-aralkyl, ($C_1$-$C_8$)-alkyl-($C_6$-$C_{18}$)-aryl, ($C_3$-$C_8$)-cycloalkyl, ($C_1$-$C_8$)-alkyl-($C_3$-$C_8$)-cycloalkyl, ($C_3$-$C_8$)-cycloalkyl-($C_1$-$C_8$)-alkyl or $R^3$ and $R^4$ together form a ($C_2$-$C_5$)-alkylene bridge.

15. The process of claim 14, wherein $R^1$ is H.

16. The process of claim 14, wherein $R^1$ is ($C_1$-$C_8$)-alkyl.

17. The process of claim 14, wherein either $R^3$ or $R^4$ is a ($C_1$-$C_8$)-alkyl.

18. The process of claim 14, wherein the reaction is carried out in a halogenated organic solvent.

19. The process of claim 14, wherein said reaction is carried out at 20-100° C.

20. The process of claim 18, wherein said reaction is carried out at 20-100° C.

* * * * *